US008729014B2

(12) United States Patent
Courcambeck et al.

(10) Patent No.: US 8,729,014 B2
(45) Date of Patent: May 20, 2014

(54) SPECIFIC HCV NS3 PROTEASE INHIBITORS

(75) Inventors: Jerome Courcambeck, Marseille (FR);
Philippe Halfon, Marseille (FR);
Mourad Bouzidi, Marseille (FR);
Steven J. Coats, McDonough, GA (US);
Richard Anthony Whitaker,
Loganville, GA (US)

(73) Assignees: RFS Pharma, LLC, Tucker, GA (US);
Genoscience, Marseille (FR)

( * ) Notice: Subject to any disclaimer, the term of this patent is extended or adjusted under 35 U.S.C. 154(b) by 291 days.

(21) Appl. No.: 13/284,641

(22) Filed: Oct. 28, 2011

(65) Prior Publication Data

US 2012/0129765 A1    May 24, 2012

Related U.S. Application Data

(60) Provisional application No. 61/408,989, filed on Nov. 1, 2010.

(51) Int. Cl.
*A61K 38/06* (2006.01)
*C07K 5/083* (2006.01)

(52) U.S. Cl.
USPC .......................... 514/4.3; 514/20.3; 530/331

(58) Field of Classification Search
None
See application file for complete search history.

(56) References Cited

U.S. PATENT DOCUMENTS

| | | | |
|---|---|---|---|
| 6,265,380 B1 | 7/2001 | Tung et al. | |
| 6,767,991 B1 | 7/2004 | Llinas-Brunet et al. | |
| 7,041,698 B2 | 5/2006 | Ripka et al. | |
| 7,189,755 B2 | 3/2007 | Sharma et al. | |
| 7,323,447 B2 | 1/2008 | Sin et al. | |
| 7,494,988 B2 | 2/2009 | Perni et al. | |
| 7,635,683 B2 | 12/2009 | Gai et al. | |
| 7,781,474 B2 | 8/2010 | Seiwert et al. | |
| 2005/0272663 A1 | 12/2005 | Arasappan et al. | |
| 2006/0183694 A1 | 8/2006 | Sin et al. | |
| 2008/0287449 A1 | 11/2008 | Niu et al. | |
| 2009/0124661 A1 | 5/2009 | Holloway et al. | |
| 2009/0176858 A1 | 7/2009 | Niu et al. | |
| 2009/0197888 A1 | 8/2009 | Gai et al. | |
| 2009/0269305 A1 | 10/2009 | Seiwert et al. | |
| 2009/0304631 A1 | 12/2009 | Campbell et al. | |
| 2010/0020939 A1 | 1/2010 | Yoshida et al. | |
| 2010/0041591 A1 | 2/2010 | Niu et al. | |
| 2010/0209391 A1 | 8/2010 | Seiwert et al. | |
| 2011/0183895 A1 | 7/2011 | Zhan | |
| 2012/0129765 A1 | 5/2012 | Courcambeck et al. | |
| 2012/0330019 A1 | 12/2012 | Wang et al. | |

FOREIGN PATENT DOCUMENTS

| | | |
|---|---|---|
| RU | 2315039 C1 | 1/2008 |
| WO | 9500536 A1 | 1/1995 |
| WO | 2005007601 A2 | 1/2005 |
| WO | 2005073216 A2 | 8/2005 |
| WO | 2006086381 A2 | 8/2006 |
| WO | 2007089618 A2 | 8/2007 |

OTHER PUBLICATIONS

Njoroge et al. "Challenges in Modern Drug Discovery: A Case Study of Boceprevir, an HCV Protease Inhibitor for the Treatment of Hepatitis C Virus Infection," Accounts of Chemical Research 50-59 Jan. 2008 vol. 41, No. 1.*
Rautio et al. "Prodrugs: design and clinical applications" Nature Reviews—Drug Discovery, vol. 7, Mar. 2008, pp. 255-270.*
Griesser "The Importance of Solvates" Polymorphism: in the Pharmaceutical Industry. Edited by Rolf Hilfiker Copyright © 2006 Wiley-VCH Verlag GmbH & Co. KGaA, Weinheim, pp. 211-233.*
Munir et al. "Hepatitis C Treatment: current and future perspectives" Virology Journal 2010, 7, pp. 296-301.*
Patel et al. "Epidemiology, Surveillance, and Prevention of Hepatitis C Virus Infections in Hemodialysis Patients" American Journal of Kidney Diseases, vol. 56, No. 2 (Aug.), 2010: pp. 371-378.*
Hagan et al. "A Systematic Review and Meta-Analysis of Interventions to Prevent Hepatitis C Virus Infection in People Who Inject Drugs" JID 2011:204 (Jul. 1), pp. 74-83.*
"2GVF: HCV NS3-4A protease domain complexed with a macrocyclic ketoamide inhibitor, SCH419021", "Protein Data Bank", May 2, 2006, pp. 1-2, Publisher: Research Collaboratory for Strucutural Bioinformatics.

* cited by examiner

*Primary Examiner* — Christina Bradley
(74) *Attorney, Agent, or Firm* — Hultquist, PLLC; Steven J. Hultquist; David Bradin

(57) ABSTRACT

The present invention is directed to compounds, compositions and methods for treating or preventing viral infections, in particular, HCV in human patients or other animal hosts.

20 Claims, No Drawings

SPECIFIC HCV NS3 PROTEASE INHIBITORS

FIELD OF THE INVENTION

The present invention is directed to compounds methods and compositions that are useful as inhibitors of the hepatitis C virus (HCV) NS3 protease, the synthesis of such compounds, and the use of such compounds for treating HCV infection and or reducing the likelihood or severity of symptoms of HCV infection.

This application claims priority to U.S. Provisional Application No. 61/408,989, filed on Nov. 1, 2010, the contents of which are hereby incorporated by reference for all purposes.

BACKGROUND OF THE INVENTION

Hepatitis C virus (HCV) has infected more than 180 million people worldwide. It is estimated that three to four million persons are newly infected each year, 70% of whom will develop chronic hepatitis. HCV is responsible for 50-76% of all liver cancer cases, and two thirds of all liver transplants in the developed world. Standard therapy (pegylated interferon alpha plus ribavirin) is only effective in 50-60% of patients; however, its effectiveness is not well understood and it is associated with significant side-effects. Therefore, there is an urgent need for new drugs to treat and/or cure HCV (1: Chen K X, Njoroge F G. A review of HCV protease inhibitors. *Curr Opin Investig Drugs.* 2009 8, 821-37; 2: Garg G, Kar P. Management of HCV infection: current issues and future options. *Trop Gastroenterol.* 2009 30, 11-8; 3: Pereira A A, Jacobson I M. New and experimental therapies for HCV. *Nat Rev Gastroenterol Hepatol.* 2009 7, 403-11).

The HCV genome comprises a positive-strand RNA enclosed in a nucleocapsid and lipid envelope and consists of 9.6 kb ribonucleotides, which encodes a large polypeptide of about 3000 amino acids (Dymock et al. Antiviral Chemistry & Chemotherapy 2000, 11, 79). Following maturation, this polypeptide is cut into at least 10 proteins. The NS3 serine protease, located in the N-terminal domain of the NS3 protein, mediates all of the subsequent cleavage events downstream in the polyprotein. Because of its role, the NS3 serine protease is an ideal drug target and previous research has shown hexapeptides as well as tripeptides show varying degrees of inhibition, as discussed in U.S. patent applications US2005/0020503, US2004/0229818, and US2004/00229776. Macrocyclic compounds that exhibit anti-HCV activity have also been disclosed in International patent applications nos. WO20061119061, WO2007/015855 and WO2007/016441 (all Merck & Co., Inc.).

The discovery of novel antiviral strategies to selectively inhibit HCV replication has long been hindered by the lack of convenient cell culture models for the propagation of HCV. This hurdle has been overcome first with the establishment of the HCV replicon system in 1999 (Bartenschlager, R., *Nat. Rev. Drug Discov.* 2002, 1, 911-916 and Bartenschlager, R., *J. Hepatol.* 2005, 43, 210-216) and, in 2005, with the development of robust HCV cell culture models (Wakita, T., et al., *Nat. Med.* 2005, 11, 791-6; Zhong, J., et al., *Proc. Natl. Acad. Sci. U.S.A.* 2005, 102, 9294-9; Lindenbach, B. D., et al., *Science* 2005, 309, 623-6).

It would be advantageous to provide new antiviral or chemotherapy agents, compositions including these agents, and methods of treatment using these agents, particularly to treat drug resistant or mutant viruses. The present invention provides such agents, compositions and methods.

SUMMARY OF THE INVENTION

The present invention provides compounds, methods and compositions for treating or preventing HCV infection in a host. The compounds have the following general formula:

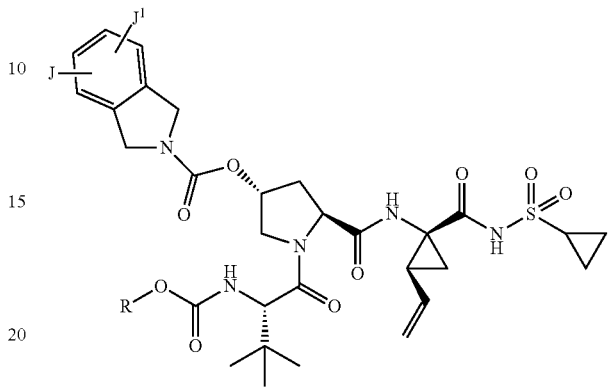

Where R, J, and $J^1$ are as defined hereinbelow.

The methods involve administering a therapeutically or prophylactically-effective amount of at least one compound as described herein to treat or prevent an infection by, or an amount sufficient to reduce the biological activity of HCV infection. The pharmaceutical compositions include one or more of the compounds described herein, in combination with a pharmaceutically acceptable carrier or excipient, for treating a host with HCV. The formulations can further include at least one further therapeutic agent. In addition, the present invention includes processes for preparing such compounds.

Hepatitis C replicons require viral helicase, protease, and polymerase to be functional in order for replication of the replicon to occur. The replicons can be used in high throughput assays, which evaluate whether a compound to be screened for activity inhibits the ability of HCV helicase, protease, and/or polymerase to function, as evidenced by an inhibition of replication of the replicon.

DETAILED DESCRIPTION

The compounds described herein show inhibitory activity against HCV. Therefore, the compounds can be used to treat or prevent a viral infection in a host, or reduce the biological activity of the virus. The host can be a mammal, and in particular, a human, infected with HCV. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The terms "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$ In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moeities. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, sulfur, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process described herein for preparing the compounds, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring or a combination of two or more heteroatoms (O, S, N, P) in an aromatic system. Both five membered and six membered ring heteroaryls are contemplated herein, as are five and six membered ring heteroaryls linked to a benzene ring, such as benzofuran, benzthiophene, benzopyrrole, and the like.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "peptide" refers to various natural or synthetic compounds containing two to one hundred amino acids linked by the carboxyl group of one amino acid to the amino group of another.

The term "pharmaceutically acceptable salt or prodrug" is used throughout the specification to describe any pharmaceutically acceptable form of a compound that upon administration to a patient, provides the parent compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compound

The compounds described herein have the following general formula:

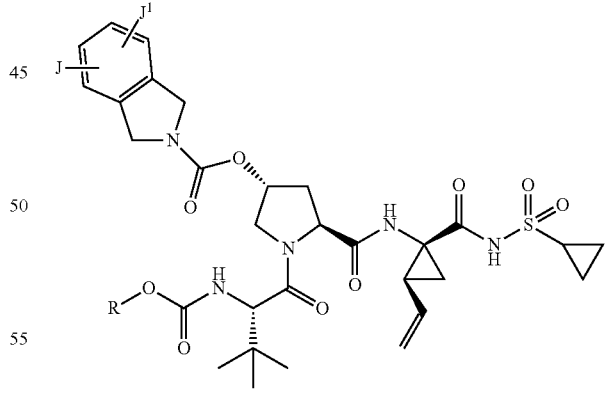

or a pharmaceutically acceptable salt or prodrug thereof, wherein

J and $J^1$ can be present or absent, and when present, are independently selected from lower alkyl ($C_1$-$C_6$), aryl, aralkyl, alkoxy, aryloxy, heterocyclyl, heterocyclyloxy, keto, hydroxy, amino, arylamino, carboxyalkyl, carboxamidoalkyl, halo, cyano, formyl, sulfonyl, or sulfonamido; and R is $C_1$-$C_{10}$ alkyl, $C_{3-8}$ cycloalkyl, aryl, heteroaryl, or heterocyclyl.

III. Stereoisomerism and Polymorphism

The compounds described herein may have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically active starting materials, by chiral synthesis, or by chromatographic separation using a chiral stationary phase or by enzymatic resolution.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Compound Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium, magnesium) salts of carboxylic acids can also be made.

V. Methods of Treatment

Hosts, including but not limited to humans, infected with HCV or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

VI. Combination or Alternation Therapy

In one embodiment, the compounds of the invention can be employed together with at least one other antiviral agent.

Table of anti-HCV Compounds Approved or in Preclinical and Clinical Development

| Drug Name | Drug Category | Pharmaceutical Company |
|---|---|---|
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/ LY 570310 | Protease Inhibitor | Vertex/Eli Lilly |
| ISIS 14803 | Antisense | Isis Pharmaceutical/ Elan |
| IDN-6556 | Caspase inhibitor | Idun Pharmaceuticals, Inc. http://www.idun.com |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wye |
| CH-6 | Serine Protease | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monclonal Antibody | XTL |
| IC41 | Therapeutic Vaccine | Intercell |
| Medusa Interferon | Longer acting interferon | Flamel Technologies |
| E-1 | Therapeutic Vaccine | Innogenetics |
| Multiferon | Long Acting Interferon | Viragen |
| BILN 2061 | Serine Protease | Boehringer - Ingelheim |
| Interferon beta-1a (REBIF) | Interferon | Ares-Serono |

VII. Pharmaceutical Compositions

Hosts, including but not limited to humans, infected with hepatitis C virus ("HCV"), or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound will be in the range of between about 0.1 and about 100 mg/kg, more generally, between about 1 and 50 mg/kg, and, preferably, between about 1 and about 20 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3,000 mg, preferably 70 to 1400 mg of active ingredient per unit dosage form. An oral dosage of 50-1,000 mg is usually convenient.

Ideally the active ingredient should be administered to achieve peak plasma concentrations of the active compound from about 0.2 to 70 μM, preferably about 1.0 to 15 μM. This can be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil.

In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

| | |
|---|---|
| aq | aqueous |
| CDI | carbonyldiimidazole |
| DMF | N,N-dimethylformamide |
| DMSO | dimethylsulfoxide |

-continued

| | |
|---|---|
| EDC | 1-ethyl-3-(3-dimethyllaminopropyl) carbodiimide hydrochloride |
| EtOAc | ethyl acetate |
| h | hour/hours |
| HOBt | N-hydroxybenzotriazole |
| M | molar |
| min | minute |
| rt or RT | room temperature |
| TBAT | tetrabutylammonium triphenyldifluorosilicate |
| TBTU | O-(Benzotriazol-1-yl)-N,N,N',N'-tetramethyluronium tetrafluoroborate |
| THF | tetrahydrofuran |

IX. General Procedures for Preparing Active Compounds

Methods for the preparation of the compounds of this invention can be prepared as described in detail below in the "Specific Example" section, or by other methods known to those skilled in the art. It will be understood by one of ordinary skill in the art that these schemes are in no way limiting and that variations of detail can be made without departing from the spirit and scope of the present invention.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Reagents and solvents were obtained from commercial suppliers and were used without further purification. Methylene chloride was dried and distilled over $CaCl_2$ and stored over molecular sieves 4 Å under argon. Tetrahydrofuran was dried over sodium/benzophenone ketyl under argon and distilled prior to use. Flash chromatography purifications were performed on Macherey Nalgel silica gel (40-63 µM) as the stationary phase or were conducted using packed RediSep® columns on a Teledyne Isco Combiflash® Companion® apparatus. Analytical High Performance Liquid Chromatography-mass analysis (HPLC-MS):

HPLC-MS conditions A1: HPLS-MS were performed on a Waters Alliance 2790 apparatus equipped with Photodiode Array Detector Waters 996 and a Waters Micromass Q-Tof using a BDS Hypersil 50×2.1, 3 µm. Eluting conditions comprised a linear gradient: 0% to 80% of $MeCN/H_2O$ in 20 minutes (containing 0.1% TFA in positive mode and without TFA in negative mode), flow rate 0.2 mL/min.

HPLC-MS conditions A2: HPLS-MS were performed on a Waters Alliance 2790 apparatus equipped with Photodiode Array Detector Waters 996 and a Waters Micromass Q-Tof using a Nucleodur C18 Pyramid 50×2.1, 3 µm. Eluting conditions comprised a linear gradient: 0% to 80% of $MeCN/H_2O$ in 20 minutes (containing 0.1% TFA in positive mode and without TFA in negative mode), flow rate 0.3 mL/min.

HPLC-MS conditions B: HPLS-MS were performed on a Agilent HP-1100 apparatus equipped with Photodiode Array Detector Agilent G1315A, a polymerlabs ELS2100 (DEDL) detector and a Agilent Simple Quad ESI for mass analysis using a Agilent Zorbax XDB-C18 RP C18 45×4.6, 3.5 µm. Eluting conditions comprised a linear gradient: 10% to 100% in 4.5 minutes of MeCN/H$_2$O (containing 0.05% TFA), flow rate 1.5 mL/min.

Low resolution mass spectra (MS) were obtained from an Applied Biosystems SCIEX 3200 QTRAP in Atmospheric Pressure Ionization condition (API) in positive (ES+) or negative (ES−) mode.

High Resolution Mass Spectroscopy (HRMS) was obtained from a Perkin Elmer apparatus.

NMR spectra were recorded on Bruker Avance 250 at 250 MHz for $^1$H and 63 MHz for $^{13}$C NMR in deuterared solvents and are referenced in ppm relative to the solvent residual peak (see reference Gottlieb H. E. et al. *J. Org Chem* 1997 (2) 7512-7515).

Example 1

Synthesis of P2 Hydroxyproline Derivative

Scheme 1: Chemical pathway to P2 hydroxyproline derivative

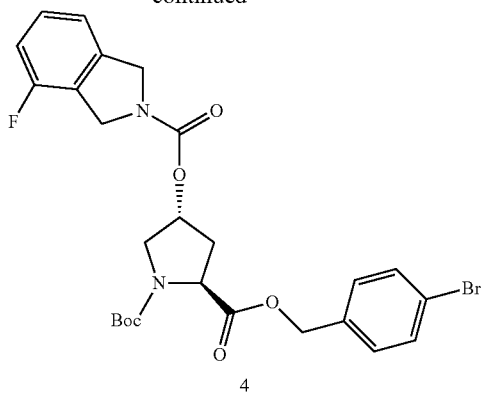

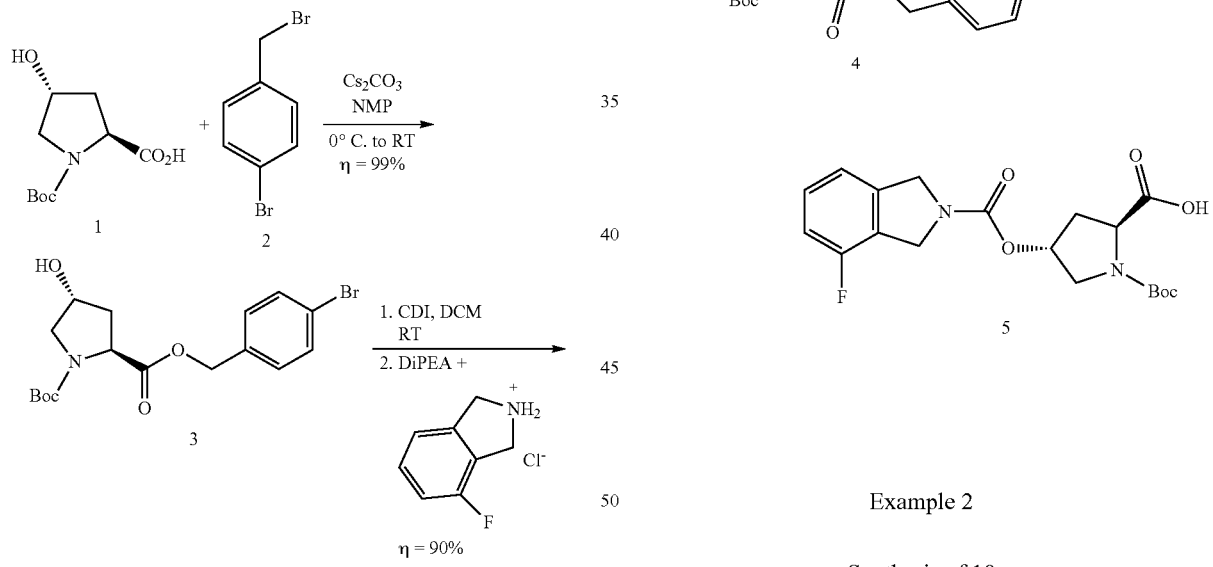

Example 2

Synthesis of 10

Scheme 2: Chemical pathway to 10

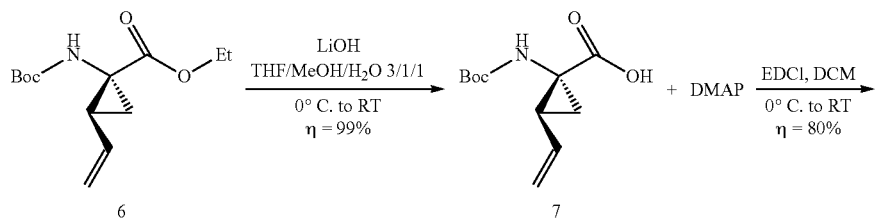

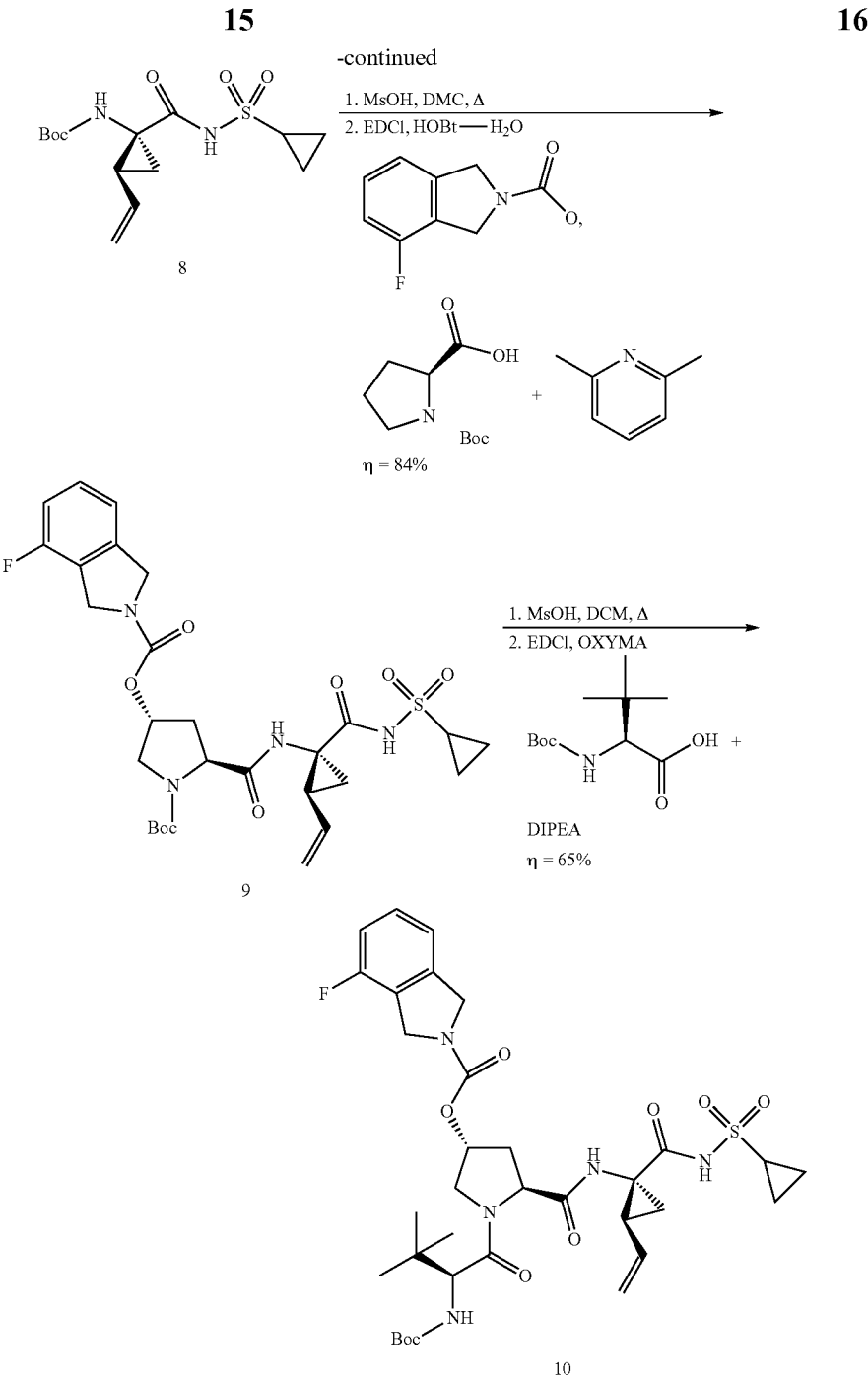

Analogs of Compound 10, in which J and J¹ are present, can be prepared, for example, by using a substituted form of the starting material:

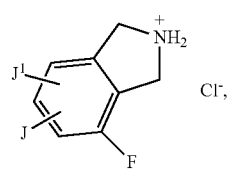

where J and J¹ are as defined herein, or, where these moieties would interfere with the coupling chemistry described in Scheme I, are protected groups that can be converted to the desired J and J¹ moieties after the coupling chemistry is completed, or at a later step in the overall synthesis.

Compounds of this formula are known, and can be prepared using no more than routine experimentation. Those skilled in the art will readily understand that incorporation of substituents onto the aryl ring can be readily realized, either before the core structures are prepared, or afterward (i.e., the substituents can be present during key coupling steps, or can be added after the unsubstituted compound (i.e., without the J and/or J¹ moieties) has been prepared. Such substituents can provide useful properties in and of themselves, or serve as a handle for further synthetic elaboration. One proviso is that such substitution should either survive the synthesis conditions, or should be added after the synthesis is otherwise complete.

For example, the aryl ring can be halogenated using various known procedures, which vary depending on the particular halogen. Examples of suitable reagents include bromine/water in concentrated HBr, thionyl chloride, pyr-ICl, fluorine and Amberlyst-A. A number of other analogs, bearing substituents in a diazotized position of an aryl ring, can be synthesized from the corresponding aniline compounds, via the diazonium salt intermediate. The diazonium salt intermediates can be prepared using known chemistry, for example, treatment of aromatic amines such as aniline with sodium nitrite in the presence of a mineral acid.

Diazonium salts can be formed from anilines, which in turn can be prepared from nitrobenzenes (and analogous amine-substituted heteroaryl rings can be prepared from nitro-substituted heteroaryl rings). The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. Likewise, alkoxy analogues can be made by reacting the diazonium salt with alcohols. The diazonium salt can also be used to synthesize cyano or halo compounds, as will be known to those skilled in the art. Mercapto substitutions can be obtained using techniques described in Hoffman et al., *J. Med. Chem.* 36: 953 (1993). The mercaptan so generated can, in turn, be converted to an alkylthio substitutuent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, *Org. React.* (*N.Y.*) 42: 335 (1992) and Hughes, *Org. Prep. Proced. Int.* 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

The substituents described above can therefore be added to the starting benzene ring, and incorporated into the final compounds described herein.

Example 3

Mitochondrial Toxicity Assays in HepG2 Cells:
i) Effect of compounds on Cell Growth and Lactic Acid Production: The effect on the growth of HepG2 cells was determined by incubating cells in the presence of 0 µM, 0.1 µM, 1 µM, 10 µM and 100 µM drug. Cells ($5 \times 10^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells"Antimicrob. Agents Chemother. 2000; 44: 496-503. To measure the effects of compounds on lactic acid production, HepG2 cells from a stock culture were diluted and plated in 12-well culture plates at $2.5 \times 10^4$ cells per well. Various concentrations (0 µM, 0.1 µM, 1 µM, 10 µM and 100 µM) of test compound were added, and the cultures were incubated at 37° C. in a humidified 5% $CO_2$ atmosphere for 4 days. At day 4 the number of cells in each well was determined and the culture medium collected. The culture medium was filtered, and the lactic acid content in the medium determined using a colorimetric lactic acid assay (Sigma-Aldrich). Since lactic acid product can be considered a marker for impaired mitochondrial function, elevated levels of lactic acid production detected in cells grown in the presence of test compound would indicate a drug-induced cytotoxic effect.

ii) Effect on compounds on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob.

Agents Chemother. 2002; 46: 3854-60). This assay was used in all studies described in this application that determine the effect of test compound on mitochondrial DNA content. In this assay, low-passage-number HepG2 cells were seeded at 5,000 cells/well in collagen-coated 96-well plates. Compounds were added to the medium to obtain final concentrations of 0 μM, 0.1 μM, 10 μM and 100 μM. On culture day 7, cellular nucleic acids were prepared by using commercially available columns (RNeasy 96 kit; Qiagen). These kits co-purify RNA and DNA, and hence, total nucleic acids were eluted from the columns. The mitochondrial cytochrome c oxidase subunit II (COXII) gene and the β-actin or rRNA gene were amplified from 5 μl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3', 5'-tetrachloro-6- carboxyfluorescein-TCCTCATCGCCCTC-CCATCCC-TAMRA-3' and 5'-CGTCTGTTATGTAAAG-GATGCGT-3'. For exon 3 of the β-actin gene (GenBank accession number E01094) the sense, probe, and antisense primers are 5'-GCGCGGCTACAGCTTCA-3',5'-6-FAM-CACCACGGCCGAGCGGGATAMRA-3' and 5'-TCTCCT-TAATGTCACGCACGAT-3', respectively. The primers and probes for the rRNA gene are commercially available from Applied Biosystems. Since equal amplification efficiencies were obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample–CT for target control)–(CT for average reference test–CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

iii) Electron Microscopic Morphologic Evaluation: NRTI induced toxicity has been shown to cause morphological changes in mitochondria (e.g., loss of cristae, matrix dissolution and swelling, and lipid droplet formation) that can be observed with ultrastructural analysis using transmission electron microscopy (see Cui L, Schinazi R F, Gosselin G, Imbach J L. Chu C K, Rando R F, Revankar G R, Sommadossi J P. Effect of enantiomeric and racemic nucleoside analogs on mitochondrial functions in HepG2 cells. Biochem. Pharmacol. 1996, 52, 1577-1584; Lewis W, Levine E S, Griniuviene B, Tankersley K O, Colacino J M, Sommadossi J P, Watanabe K A, Perrino F W. Fialuridine and its metabolites inhibit DNA polymerase gamma at sites of multiple adjacent analog incorporation, decrease mtDNA abundance, and cause mitochondrial structural defects in cultured hepatoblasts. Proc Natl Acad Sci USA. 1996; 93: 3592-7; Pan-Zhou X R, L Cui, X J Zhou, J P Sommadossi, V M Darley-Usmar. Differential effects of antiretroviral nucleoside analogs on mitochondrial function in HepG2 cells. *Antimicrob. Agents Chemother.* 2000, 44, 496-503). For example, electron micrographs of HepG2 cells incubated with 10 μM fialuridine (FIAU; 1,2'-deoxy-2'-fluoro-1-D-arabinofuranosly-5-iodo-uracil) showed the presence of enlarged mitochondria with morphological changes consistent with mitochondrial dysfunction. To determine if compounds promoted morphological changes in mitochondria, HepG2 cells ($2.5 \times 10^4$ cells/mL) were seeded into tissue cultures dishes (35 by 10 mm) in the presence of 0 μM, 0.1 μM, 1 μM, 10 μM and 100 μM test compound. At day 8, the cells were fixed, dehydrated, and embedded in Eponas described previously. Thin sections were prepared, stained with uranyl acetate and lead citrate, and then examined using transmission electron microscopy.

Example 4

Assay for Bone Marrow Cytotoxicity

Primary human bone marrow mononuclear cells were obtained commercially from Cambrex Bioscience (Walkersville, Md.). CFU-GM assays were carried out using a bilayer soft agar in the presence of 50 units/mL human recombinant granulocyte/macrophage colony-stimulating factor, while BFU-E assays used a methylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl)guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of Cytotoxicity of the (−) and (+) enantiomer of 2',3'-dideoxy-3'-thiacytidine in normal human bone marrow progenitor cells. Biochem. Pharmacol. 1992; 44:1921-1925). Each experiment was performed in duplicate in cells from three different donors. AZT was used as a positive control. Cells were incubated in the presence of the compound for 14-18 days at 37° C. with 5% $CO_2$, and colonies of greater than 50 cells are counted using an inverted microscope to determine $IC_{50}$. The 50% inhibitory concentration ($IC_{50}$) was obtained by least-squares linear regression analysis of the logarithm of drug concentration versus BFU-E survival fractions. Statistical analysis was performed with Student's t test for independent non-paired samples.

Example 5

Cytotoxicity Assay

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity $IC_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25,1-11).

The data for 10 is

PBM>100 μM (17% inhibition@100 μM)
CEM>100 μM (11% inhibition@100 μM)
VERO>100 (−0.8% inhibition@100 μM)

Example 6

HCV Replicon Assay[1]

Huh 7 Clone B cells containing HCV replicon RNA would be seeded in a 96-well plate at 5000 cells/well, and the compounds tested at 10 µM in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds was also calculated by using the ΔCt rRNA values. (2'-Me-C) was used as the control. To determine $EC_{90}$ and $IC_{50}$ values[2], ΔCt: values were first converted into fraction of starting material[3] and then were used to calculate the % inhibition.

References
1. Stuyver L et al., Ribonucleoside analogue that blocks replication or bovine viral diarrhea and hepatitis C viruses in culture. *Antimicrob. Agents Chemother.* 2003, 47, 244-254.
2. Reed I J & Muench H, A simple method or estimating fifty percent endpoints. *Am. J. Hyg.* 27: 497, 1938.
3. Applied Biosystems Handbook The results are shown in Table 1 below:

TABLE 1

| Compound | Conc (µM) | DCt HCV | DCt rRNA | HCV | rRNA | EC50 | EC90 | CC50 |
|---|---|---|---|---|---|---|---|---|
| 10 | 0.01 | 1.16 | −0.21 | 54.99 | −15.99 | 0.01 | 0.03 | >0.3 |
|  | 0.03 | 3.29 | −0.49 | 89.67 | −40.10 |  |  |  |
|  | 0.1 | 6.05 | −0.09 | 98.47 | −6.27 |  |  |  |
|  | 0.3 | 8.72 | 0.14 | 99.76 | 9.35 |  |  |  |

Example 7

Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives compound at a dose level of 2-20 mg/kg, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1,2, 3,6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (Tmax), area under the curve (AUC), half-life of the dosage concentration (TV,), clearance (CL), steady state volume and distribution (Vss) and bioavailability (F).

Example 8

Effect of HCV Protease Inhibitors on Selected Human Proteases

HCV protease inhibitors have demonstrated great antiviral potency in addition to interesting toxicities associated with inhibition of host proteases. In an effort to circumvent similar toxicities, new protease inhibitors were evaluated for inhibition of a panel of important human proteases. The enzymes tested are Elastase (Neutrophil), Plasmin, Thrombin, and Cathepsin S.

Neutrophil elastase (or leukocyte elastase) also known as ELA2 (elastase 2) is a serine protease in the same family as chymotrypsin and has broad substrate specificity. Secreted by neutrophils during inflammation, one of its primary roles is to destroy bacteria in host tissue. (Belaaouaj et al, Science 289 (5482): 1185-8).

Plasmin is a serine protease derived from the conversion of plasminogen in blood plasma by plasminogen activators (Collen, D. *Circulation,* 93, 857 (1996). This enzyme (EC 3.4.21.7) degrades many blood plasma proteins, most notably, fibrin clots. Plasmin is also involved in several pathological and physiological processes such as inflammation, neoplasia, metastasis, wound healing, angiogenesis, embryogenesis and ovulation (Vassalli, J. D. et al, *J. Clin. Invest.* 88, 1067 (1991).

Thrombin is a coagulation protein in the blood stream that has many effects in the coagulation cascade, the last enzyme in the clotting cascade. It is a serine protease that converts soluble fibrinogen into insoluble strands of fibrin, as well as catalyzing many other coagulation-related reactions.

Cathepsin S, a member of the peptidase C1 family, is a lysosomal cysteine protease that may participate in the degradation of antigenic proteins to peptides for presentation on MHC class II molecules, therefore it is key to immune response. The encoded protein can function as an elastase over a broad pH range.

Materials:
  Victor 3 Plate reader (Perkin Elmer)
  Clear 96 well Plates (Phenix Research)
  Black 96 well Plates (Perkin Elmer)
  RNase and Dnase pure water
Methods:
  Elastase (Human Neutrophil (Cat #16-14-051200 Athens Research and Technology, Athens Ga.)): Reactions were conducted in a sample volume of 100 μL per well in a clear 96 well plate. A 2× assay buffer was made containing 200 mM Tris-HCl (pH 7.5), 150 mM NaCl and 50% glycerol. For each sample 50 μL 2× assay buffer was added to each well. The substrate (MeOSuc-AAPV-pNA, Chromogenic Substrate, Cat #P-213, Enzo Life Sciences, Plymouth Meeting, Pa.; 50 mM stock in DMSO) was added to a final concentration of 1 mM. The drug dilutions were added (25 μL) at 4× concentrations in water. Finally, a mixture was made of 1 μL elastase and 22 μL water for each sample and 23 μL was added to each well. The samples were incubated at room temperature for 30 min. The absorbance at 405 nM was read on the Victor 3 plate reader. All samples were tested in duplicate. Results are shown as blank adjusted (no Elastase) percentages of maximum absorbance, which was given by a no inhibitor control.

Plasmin and Thrombin (Sensolyte RH110 Plasmin Activity Assay Kit and Sensolyte Thrombin Activity Assay Kit (Anaspec)): Reactions were conducted in a sample volume of 100 μL per well in a black 96 well plate. Protocol A was followed from the kit insert where the 2× assay buffer was diluted 1:1 with deionized water. Included in each assay were a positive control (diluted enzyme and no test compound), inhibitor control (contains diluted enzyme and plasmin inhibitor; component E from the kit or thrombin inhibitor; N-α-NAPAP synthetic inhibitor) and substrate control (assay buffer and substrate). Vehicle and autofluorescence controls were also performed. Drug dilutions were added (10 μL) at 10× concentrations in assay buffer. The enzyme was added at 40 μL/well at a concentration of 0.25 μg/mL (plasmin) and 1 μg/mL (thrombin) to all wells except the substrate control. Finally, 50 μL assay buffer containing substrate was added to each well. The substrate was added to a final concentration of 50 nM (plasmin) or 20 nM (Thrombin). The samples were incubated at room temperature for 30 min. The fluorescence intensity was read on the Victor 3 plate reader at Ex/Em=490 nm/520 nm. All samples were tested in duplicate. Results are shown as substrate control adjusted percentages of maximum absorbance, which was given by the positive control.

Cathespsin S (Sensolyte Cathepsin S Activity Assay Kit (Anaspec)): Reactions were conducted in a sample volume of 100 μL per well in a black 96 well plate. Protocol A was followed from the kit insert where DTT was added to assay buffer to yield a 5 μM concentration. Included in each assay were a positive control (diluted enzyme and no test compound), inhibitor control (contains diluted enzyme and plasmin inhibitor; component E or thrombin inhibitor; N-a-NAPAP synthetic inhibitor) and substrate control (assay buffer and substrate). Vehicle and autofluorescence controls were also performed. Drug dilutions were added (10 μL) at 10× concentrations in assay buffer. The cathepsin S was added at 40 μL/well at a concentration of 2.5 μg/mL to all wells except the substrate control. Finally, 50 82 L of assay buffer containing substrate was added to each well. The substrate was added to a final concentration of 16 nM. The samples were incubated at room temperature for 30 min. The fluorescence intensity was read on the Victor 3 plate reader at Ex/Em=490 nm/520 nm. All samples were tested in duplicate. Results are shown as substrate control adjusted percentages of maximum absorbance, which was given by the positive control.

The results are shown in Table 2, below:

TABLE 2

| | | | | Inhibition of Human Proteases ($IC_{50}$, μM) | | | | |
|---|---|---|---|---|---|---|---|---|
| Drug | Elastase | Cathepsin G | Chymo-trypsin | Kallikrein | Plasmin | Thrombin | Cathepsin S | Chymase |
| 10 | >100 | >100 | >100 | 47 | >100 | >100 | >100 | >100 |

Example 9

Activity of Compounds Versus Hepatitis C Virus NS3/4A WT and Mutant Protease

The HCV NS3/4A protease assays were carried out using a SensoLyte® 490 HCV Protease Assay Kit using fluorescence resonance energy transfer (FRET) peptide (AnaSpec).

The results are shown in Tables 3 and 4 below:

TABLE 3

| | Anti-HCV protease activity | | | | | | | | | |
|---|---|---|---|---|---|---|---|---|---|---|
| | Wild Type | | A156T | | R155K | | D168V | | V36M | |
| Code | $EC_{50}$, μM | $EC_{90}$, μM | EC50, μM | EC90, μM | EC50, μM | EC90, μM | EC50, μM | EC90, μM | EC50, μM | EC90, μM |
| 10 | 0.0049 | 0.030 | 0.033 | 0.130 | 0.27 | 2.7 | 0.040 | 0.630 | 0.0034 | 0.0455 |
| stdev | 0.0017 | 0.029 | 0.030 | NA | 0.17 | 3.0 | 0.043 | NA | 0.0037 | 0.0488 |
| Fold Increase | 1.0 | 1.0 | 6.7 | 4.4 | 55.8 | 91.4 | 8.1 | 21.1 | 0.7 | 1.5 |

TABLE 4

| | Anti-HCV protease activity | | | | | | | |
| --- | --- | --- | --- | --- | --- | --- | --- | --- |
| | A156S | | V170A | | D168A | | T54A | |
| Code | EC50, μM | EC90, μM | EC50, μM | EC90, μM | EC50, μM | EC90, μM | EC50, μM | EC90, μM |
| 10 | 0.008 | 0.085 | 0.0055 | 0.0095 | 0.57 | 8.30 | 0.07 | 0.85 |
| stdev | 0.000 | 0.021 | 0.0007 | 0.0007 | 0.01 | NA | 0.03 | NA |
| Fold Increase | 1.6 | 2.9 | 1.1 | 0.3 | 115.3 | 278.5 | 15.0 | 28.5 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I):

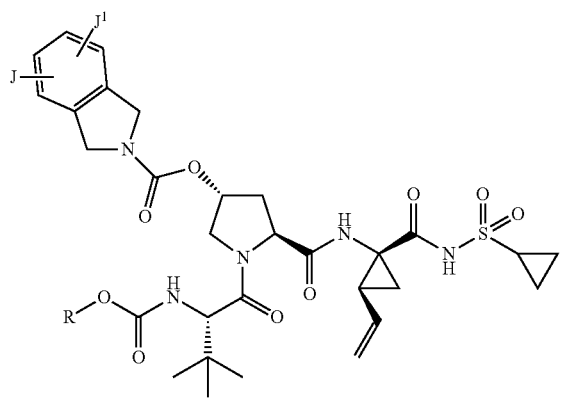

(I)

or a pharmaceutically acceptable salt, thereof, wherein
J and J¹ can be present or absent, and when present, are independently selected from the group consisting of lower alkyl ($C_1$-$C_6$), aryl, arylalkyl, alkoxy, aryloxy, heterocyclyl, heterocyclyloxy, keto, hydroxy, amino, arylamino, carboxyalkyl, carboxamidoalkyl, halo, cyano, formyl, sulfonyl, and sulfonamido; and
R is alkyl ($C_1$-$C_{10}$), cycloalkyl ($C_3$-$C_8$), aryl, heteroaryl, or heterocyclyl,
wherein the compound can be present in the form of individual enantiomers, stereoisomers, rotamers, tautomers, racemates, or mixtures thereof.

2. The compound of claim 1, wherein the compound, or pharmaceutically acceptable salt thereof, is in the form of individual enantiomers, stereoisomers, rotamers, tautomers, racemates, or mixtures thereof.

3. A method for treating an HCV infection, or reducing the biological activity of HCV, comprising administering a therapeutically effective amount of a compound of claim 1 to a patient in need of treatment thereof.

4. The method of claim 3, wherein the compound is administered in combination with another anti-HCV agent.

5. A method for inhibiting NS3 serine protease activity, comprising the step of administering a therapeutically effective amount of a compound according to claim 1 to a patient in need of treatment thereof.

6. The method of claim 3, wherein said compound is administered to a patient and is formulated together with a pharmaceutically suitable carrier into a pharmaceutically acceptable composition.

7. The method of claim 4, wherein said compound is administered to a patient and is formulated together with a pharmaceutically suitable carrier into a pharmaceutically acceptable composition.

8. The method of claim 5, wherein the compound administered to said patient is formulated together with a pharmaceutically suitable carrier into a pharmaceutically acceptable composition.

9. The compound of claim 1, wherein one of J or J¹ is F.

10. The compound of claim 1, wherein R is t-butyl.

11. The method of claim 3, wherein one of J or J¹ is F.

12. The method of claim 3, wherein R is t-butyl.

13. The method of claim 5, wherein one of J or J¹ is F.

14. The method of claim 5, wherein R is t-butyl.

15. The compound of claim 1, wherein the moiety:

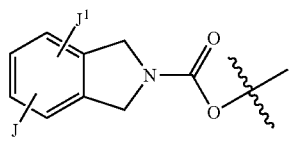

is

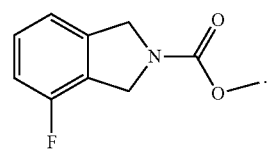

16. The method of claim 3, wherein the moiety:

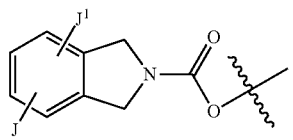

is

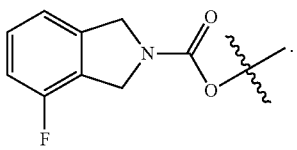 [SMILES: *OC(=O)N1Cc2cccc(F)c2C1]

17. The compound of claim 5, wherein the moiety:

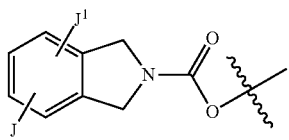

is

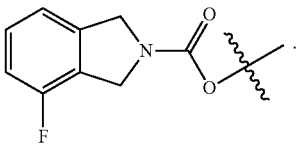 [SMILES: *OC(=O)N1Cc2cccc(F)c2C1]

18. A compound having the formula:

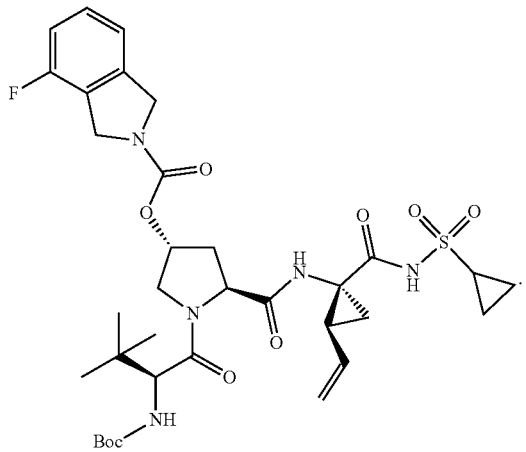 [SMILES: C=C[C@@H]1C[C@]1(NC(=O)[C@@H]1C[C@@H](OC(=O)N2Cc3cccc(F)c3C2)CN1C(=O)[C@@H](NC(=O)OC(C)(C)C)C(C)(C)C)C(=O)NS(=O)(=O)C1CC1]

19. A method for treating an HCV infection, or reducing the biological activity of HCV, comprising administering a therapeutically effective amount of a compound of claim 18 to a patient in need of treatment thereof.

20. A method for inhibiting NS3 serine protease activity, comprising the step of administering a therapeutically effective amount of a compound according to claim 18 to a patient in need of treatment thereof.

* * * * *

UNITED STATES PATENT AND TRADEMARK OFFICE
CERTIFICATE OF CORRECTION

PATENT NO. : 8,729,014 B2  
APPLICATION NO. : 13/284641  
DATED : May 20, 2014  
INVENTOR(S) : Courcambeck et al.

Page 1 of 3

It is certified that error appears in the above-identified patent and that said Letters Patent is hereby corrected as shown below:

In the Specification

Column 14-15, Scheme 2: Chemical pathway to 10: Delete

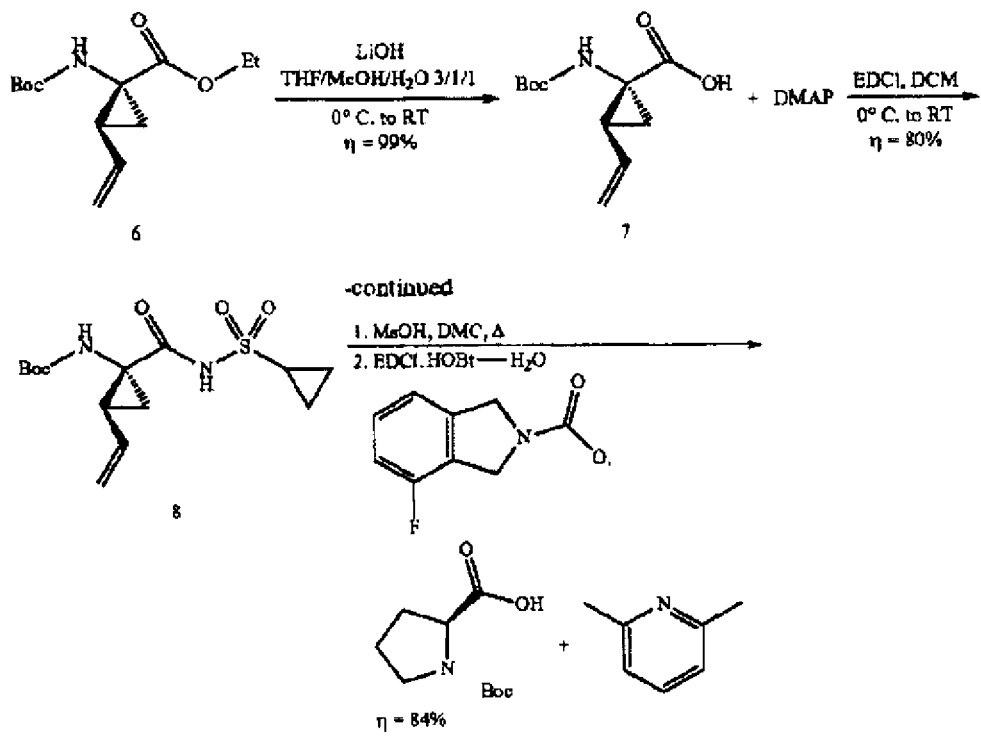

"

Signed and Sealed this
Twentieth Day of January, 2015

Michelle K. Lee
*Deputy Director of the United States Patent and Trademark Office*

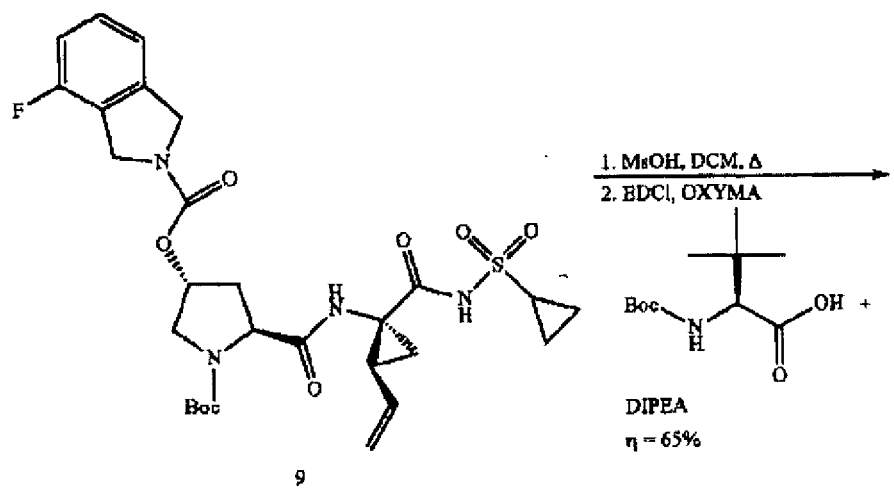
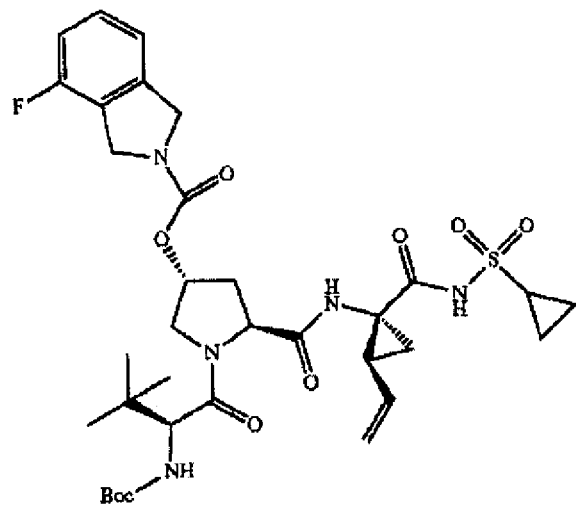
" and insert

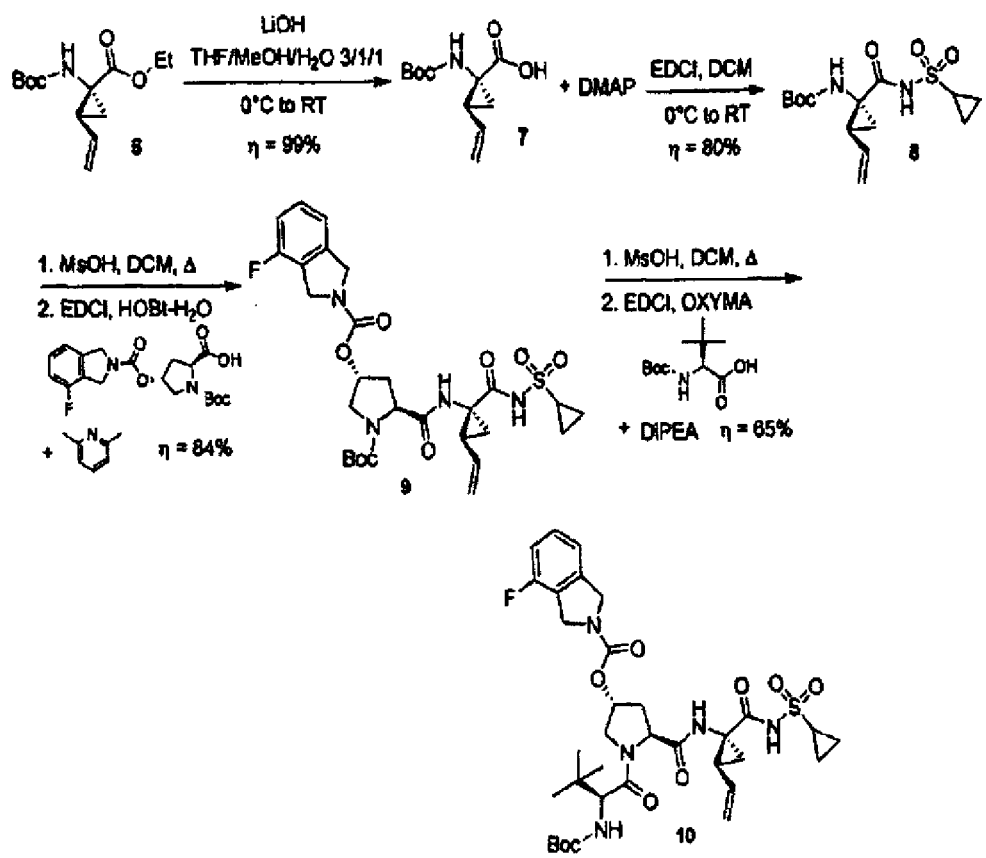
Column 24, line 21, Delete "... Finally, 50 82 L of assay ..." and insert --... Finally, 50μL of assay ...--